(12) United States Patent (10) Patent No.: US 7,544,182 B2
Kiehne (45) Date of Patent: Jun. 9, 2009

(54) SINGLE USE SYRINGE WITH IMPROVED NEEDLE RETRACTION MECHANISM

(75) Inventor: Bruce Leigh Kiehne, Springwood (AU)

(73) Assignee: Occupational & Medical Innovations Ltd, Slacks Creek, Queensland (AU)

( * ) Notice: Subject to any disclaimer, the term of this patent is extended or adjusted under 35 U.S.C. 154(b) by 237 days.

(21) Appl. No.: 11/524,891

(22) Filed: Sep. 22, 2006

(65) Prior Publication Data

US 2007/0244433 A1    Oct. 18, 2007

Related U.S. Application Data

(63) Continuation-in-part of application No. 11/218,498, filed on Sep. 6, 2005, now abandoned.

(30) Foreign Application Priority Data

May 13, 2005    (AU) .............................. 2005902427

(51) Int. Cl.
*A61M 5/00* (2006.01)
(52) U.S. Cl. .................................................. 604/110
(58) Field of Classification Search ................ 604/110, 604/181, 187, 192, 194–195; 128/919
See application file for complete search history.

(56) References Cited

U.S. PATENT DOCUMENTS

| | | | |
|---|---|---|---|
| 5,180,370 A | 1/1993 | Gillespie | |
| 5,385,551 A | 1/1995 | Shaw | |
| 5,389,076 A | 2/1995 | Shaw | |
| 5,407,436 A * | 4/1995 | Toft et al. | 604/195 |
| 5,578,011 A | 11/1996 | Shaw | |
| 5,632,733 A | 5/1997 | Shaw | |
| 5,882,342 A | 3/1999 | Cooper et al. | |
| 5,935,104 A | 8/1999 | Janek et al. | |
| 5,984,898 A | 11/1999 | Garvin | |
| 6,090,077 A | 7/2000 | Shaw | |
| 6,241,707 B1 | 6/2001 | Dysarz | |
| 6,994,690 B2 | 2/2006 | Kiehne | |

* cited by examiner

*Primary Examiner*—Nicholas D Lucchesi
*Assistant Examiner*—Theodore J Stigell
(74) *Attorney, Agent, or Firm*—Hoffman, Wasson & Gitler

(57) ABSTRACT

A single use syringe including shoot back, or retraction, mechanism for biasing a needle, retained in needle holder, back into the interior of the syringe body after use. The needle holder is urged, by a spring in the front of the syringe body, to pass through a piercable seal formed in the front fact of the piston. The needle holder comprises an inner part containing the needle, an outer part engaging the interior wall of the syringe, and a frangible portion joining the inner and outer parts. A raised portion, or bump, is formed partially about the outer part of the needle holder, facing the seal in the piston. The raised portion provides an initial contact area with the plunger, to reduce the force required to break the frangible portion and trigger the shoot-back mechanism. The raised portion may consist of an uppermost portion for contact with the plunger, and a shoulder portion adjacent the uppermost portion to reduce dead space. The edge portion of the seal is thickened, and is relatively compressible, to reduce the dead space prior to triggering the shoot-back mechanism.

12 Claims, 3 Drawing Sheets

SINGLE USE SYRINGE WITH IMPROVED NEEDLE RETRACTION MECHANISM

RELATED APPLICATIONS

The present application is a continuation-in-part application, based upon parent U.S. patent application Ser. No. 11/218,498, filed Sep. 6, 2005 now abandoned, and presently pending in Group Art Unit 3763.

FIELD OF THE INVENTION

This invention is directed to the medical field and particularly directed to a single use syringe that has a needle shoot back mechanism (retraction mechanism) with improved features.

BACKGROUND OF THE INVENTION

In the medical field, needlestick is a continuing problem. Needlestick is the term used when a contaminated needle pricks or cuts a person. A contaminated needle can readily become a source of infection. Another problem with syringes is with sharing of needles which can also result in infection.

For this reason, it is known to provide a syringe having a needle that has a particular design such that the needle can be used only once. One way that this is achieved is to retract the needle back into the syringe body after use. This also provides the other advantage of minimising needlestick injury.

Many types of single use syringes are known, and most have some form of retraction mechanism (also called a shoot back mechanism) to shoot the contaminated needle back into the syringe body after use.

It is known to provide single use syringes where the needle is spring biased and is held in place by a cuttable member. In order to ensure that the member is properly cut thereby releasing the needle, a two-part cutting action is usually required. In the two-part cutting action, the plunger typically has a forward cutting edge and the front of the needle also has some form of cutting edge and a double cutting action is required to ensure that the cuttable member is property cut to release the needle. It is found that attempting to cut a cuttable member to release a spring-biased needle is not always reliable and does not always work.

Another type of known single use syringe has a base member that grips an enlargement on the needle. The plunger pushes the base member forwardly, which further compresses a spring that is around the needle. The pushing action releases the grip between the base member and the enlargement on the needle. This allows the needle containing the enlargement to be shot back into the plunger while leaving the spring behind. The spring is initially compressed partially but then becomes compressed fully as the plunger forces the base member forwardly. This arrangement requires a needle having a special design (containing an enlargement), which means that conventional needles cannot be used.

Another type of syringe has a plunger seal which moves on the plunger and where the plunger seal slides rearwardly along a bearing surface in response to a force being applied to the seal that is in excess of the operational force of the syringe. This arrangement begins the retraction sequence of the needle. With this arrangement, a specially designed plunger seal is required which moves relative to the plunger. Conventional plungers have a plunger seal that is fixed to the plunger.

Another type of syringe has a shoot back arrangement consisting of two parts which slide relative to each other to release the needle. The two parts consist of an outer part and an inner part. The inner part holds the needle and is biased by a helical spring. The two parts are held together by frictional engagement to each other. A plunger progressively pushes the outer part forwardly thereby progressively reducing the amount of frictional engagement between the outer part and the inner part until such time that the bias of the spring is sufficient to shoot the inner part away from frictional engagement with the outer part. This arrangement requires a sliding frictional grip to hold the two-part together which is considered quite risky and requires careful manufacture.

Another arrangement uses a needle holder having an elongate body portion in front and a head end in back and providing a spring under the head end that circumscribes the needle holder. The use of an elongate body in a needle holder makes this arrangement difficult for use in small and confined spaces.

It is found that retraction (shoot back) mechanisms that use a cutting action are not particularly reliable especially for small syringes, and there would therefore be an advantage if a retraction mechanism could be used that did not require a cutting action. While not wishing to be bound by theory, the small syringes have a very small needle holding attachment, and trying to cut part of the attachment away using a knife edge on the piston is not particularly reliable. For instance, variation in the plastic used in the attachment can cause the plastic to become too rubbery, or too hard, and this can make the cutting action incomplete or unreliable.

A useful type of retraction mechanism enables the needle holder to be retracted or shot back into the hollow plunger in a relatively straightforward manner. There is a disadvantage if the retraction is impeded. It is always necessary to have some form of seal or cover over the front of the plunger and this seal or cover needs to be broken or pierced to allow the needle holder (containing the contaminated needle) to be shot back into the hollow plunger and through or past the seal or cover. It is found advantageous if the front of the plunger contains a relatively thin seal as this can improve the reliability of the shoot back mechanism. Conversely, it is found to be a disadvantage if the front of the plunger contains a stopper, a plug, or some other relatively bulky member. If a stopper or plug is used, there is no way that the needle holder can pierce through the stopper or plug, and therefore, it is necessary for the needle holder to be shot back with sufficient force to also push back the stopper or plug into the plunger body. Therefore, there would be an advantage to provide a single use syringe with a retraction mechanism that has the front of the plunger containing a relatively thin seal through which the needle holder can pass as opposed to a relatively bulky stopper or plug.

Another important consideration with single use retractable needle syringes is the force required to activate, or to trigger, the shoot back mechanism. This force is the pressure that needs to be applied to the rear of the plunger to push the plunger hard up against the needle holder to trigger release of the needle holder. Typically, this force will be applied by the user's thumb. It is found that this force can be up to 9 kg to enable a conventional shoot back needle to be triggered, and this is found to be excessive. However, simply making the shoot back mechanism more "flimsy" is not a solution, as this can result in accidental or inadvertent triggering of the shoot back mechanism. Therefore, there would be an advantage if a single use retractable needle syringe could be manufactured that would be reliable but that would also reduce the amount of force required to trigger the shoot back mechanism.

Attempts have been made to reduce the triggering force. However, previous attempts have been directed to providing a complex design to the front of the plunger. The complex design to the front of the plunger includes having a part of the plunger front face projecting forwardly from the remainder of the plunger front face. Thus, only part of the plunger (the forwardly projecting part) initially contacts the needle holder to trigger the shoot back mechanism. This type of arrangement prevents the front of the plunger from having a "conventional" design which is usually a substantially flat or planar seal extending over the otherwise open front of the plunger. As mentioned previously, there is an advantage in having a substantially "conventional" plunger head to enable the needle to be shot back through the plunger head and into the plunger body without needing to push back a stopper etc. Also, having a relatively ordinary plunger head allows the needle to shoot back through the plunger head without carrying any significant debris (from the plunger head) which can impede efficient retraction of the needle. Another advantage with having a relatively conventional plunger head design, is that the medical practitioner can more easily see the operation of the plunger and especially how close the plunger is to the end of its stroke. With a complicated plunger head design, it becomes difficult to see where the "end" of the plunger actually is with respect to the front of the syringe.

Another disadvantage with many existing single use syringes is that the mechanism required to shoot back the needle often has a portion protruding into the syringe barrel, and can result in incomplete expulsion of the liquid from the barrel and through the needle. In other words, many existing single use syringes have a "dead space" where the syringe fluid can collect and where the fluid will not be properly expelled from the syringe. This can result in incomplete or erroneous levels of fluid being injected into a person. There is therefore a significant advantage if the volume of "dead space" could be reduced, prior to triggering the shoot back mechanism. As mentioned previously, it is also advantageous to reduce the force required to trigger the shoot back mechanism. The mechanism described above to reduce the force to trigger the shoot back mechanism (the complex plunger design) results in part of the plunger front face projecting forwardly with respect to the remainder of the plunger front face. This particular design can also increase the "dead space" due to the design of the plunger.

Therefore, there would be an advantage to provide a design that can reduce the force to trigger the shoot back mechanism but which can also reduce the dead space, and which is reliable in use. The applicant considers that reliability can be provided by having a shoot back mechanism where the needle shoots through a relatively thin portion of the plunger head (therefore there is no need to push back any stopper, and there is no "shatter plate" and the like which can carry debris back into the plunger body), and where the plunger head is otherwise of a conventional type shape which is found to be best in reducing dead space and is also relatively easy to manufacture.

While there is an advantage in having a "conventional" relatively flat type plunger head to reduce dead space, this conventional shape can sometimes not be as effective as possible in reducing dead space because of the particular construction of the "reduced force" shoot back mechanism. Therefore, there would be an advantage to provide a particular construction of part of the shoot back mechanism which would reduce dead space but still allow a "conventional" type plunger head to be used.

Another disadvantage with some of the spring biased shoot back needles, is that in practice, it is possible to reassemble the mechanism which means that the syringe and needle can be reused. Clearly, a single use syringe should be manufactured in such a manner that it would be impossible to reuse the syringe. Therefore, there would be an advantage in having some form of "destructive mechanism" which would render the syringe unable to be reused.

It will be clearly understood that, if a prior art publication is referred to herein, this reference does not constitute an admission that the publication forms part of the common general knowledge in the art.

SUMMARY OF THE INVENTION

It is an object of the invention to provide a single use syringe having a shoot back mechanism which can be triggered with reduced force, and optionally which can also reduce the dead space in the syringe.

In one form, the invention resides in a single use syringe which comprises:

a syringe body which contains a front end area containing a longitudinal passageway which has a front portion and a rear portion, a plunger which contains a front face which extends into the syringe body, a pierceable seal extending over the front face of the plunger, a needle holder that is attached inside and in the front area of the syringe body, a needle that is attached to the needle holder, a spring in the front of the syringe body and that is biased to shoot the needle holder through the pierceable seal in the front face of the plunger and into the plunger, the needle holder comprising an inner part and an outer part, the inner part containing the needle, the outer part engaging with a wall of the longitudinal passageway and initially in a rear portion of the passageway, a frangible portion between the inner part and the outer part, the outer part containing a raised portion directed towards the seal of the plunger, the raised portion extending only partway about the inner portion, the raised portion functioning to provide an initial contact area of the plunger with the outer part of the needle holder, thereby reducing the force required to break the frangible portion thereby triggering the shoot back mechanism.

In a more particular form there is provided a single use syringe as described immediately above but where the raised portion contains an uppermost portion adapted for contact with the plunger, and a shoulder portion adjacent the uppermost portion and which functions to reduce dead space between the plunger head and the needle retracting mechanism.

In this more particular form, the shoulder portion can function to fill the otherwise dead space and therefore reduce the volume of dead space which may otherwise be present between the plunger head and the shoot back mechanism.

It is envisaged that the shoulder portion will be positioned adjacent each side of the uppermost portion and it is envisaged that the shoulder portion and the uppermost portion will comprise a unitary "raised portion" on the outer part.

The shoulder portion may comprise a "chamfer" trailing down from the uppermost portion to the surface of the outer part.

The shoulder portion may have a relatively smooth incline, or may have an irregular shape or any other type of shaped or configuration that can reduce the dead space while not undesirably affecting the shoot back mechanism, and especially the reduced force shoot back mechanism.

An advantage of this particular arrangement is that the plunger has a conventional flat front face and can be fitted with a pierceable seal to minimise any interference with the needle holder shooting back into the plunger body and through or past the seal. Thus, there is no requirement for a relatively bulky stopper or plug to be fitted to the front of the plunger. There is also no need for the front of the plunger to contain a cutting face. Another advantage is that the triggering mechanism uses a push and break movement where the outer part is pushed forwardly by the plunger along the longitudinal passageway while the inner part remains stationary, and this movement breaks the frangible portion that holds the inner part to the outer part. This is considered advantageous over a cutting action or any other type of triggering action. However, a main advantage is that the force required to break the frangible portion and therefore trigger the shoot back mechanism is reduced due to the design of the outer part and particularly due to the raised portion (bump) that faces the front of the plunger and which provides the initial point of contact between the plunger and the outer part. The design also can reduce dead space, as well as enabling the plunger to be fitted with a pierceable seal as opposed to the complex design of the plunger that has a forwardly projecting part and which may be difficult to contain a pierceable seal.

It is preferred that the seal that extends over the front face of the plunger contains a central portion that extends over the otherwise hollow front of the plunger, and an edge portion that extends over the edge of the plunger. The central portion can be designed to be more easily pierced or broken, for instance by making the wall thickness less.

It is preferred that the edge portion contains a thicker area of seal and this area can be compressed or squashed as it contacts the raised portion of the outer part. The advantage of this is that the front of the plunger can be pushed quite close to the needle holder (thereby reducing dead space) before the force is sufficient to trigger the shoot back mechanism. This will be described in greater detail below.

The syringe may be of any suitable shape and size. It is envisaged that the syringe will vary between a 1 mil syringe up to a 50 mil syringe or even more. The syringe may be made of any suitable material such as plastic, glass or even metal. It is preferred that the syringe is made of plastic.

The syringe has a syringe body. The body will typically be cylindrical in design as is conventional, although if necessary, the body may have other shapes such as rectangular in cross-section, oval in cross-section and the like. The length of the syringe body will vary depending on the size of the syringe and will typically be between 30-200 millimeters although this can vary. The diameter of the syringe body may also vary and will typically be between 5-20 millimeters although this can vary. The syringe body will typically have a wall thickness of between 0.3-4 mm although this can vary. The syringe body may be provided with grip enhancing features or positioning enhancing features such as outwardly extending tabs or flanges, exterior ribs and the like.

The syringe body may have a front end area from which the puncture needle will project. The front end area will typically have a front opening through which the needle can extend. The front end area will contain a longitudinal passageway which will typically be designed such that the plunger can pass along or at least partially along this passageway, and the passageway forms part of the shoot back mechanism which will be described in greater detail below. The passageway will typically have a front portion which is more towards the front opening through which the needle extends, and a rear portion. The size and shape of this passageway can vary, but it is envisaged that this passageway may comprise a continuation of the internal bore of the syringe body. The front passageway may have a length of between 5-30 mm depending on the size of the syringe.

The syringe will have a plunger. The length of the plunger will vary depending on the size of the syringe and the plunger will typically have a length of between 30-200 mm although this can vary. The plunger is designed to slide in the syringe body and therefore the plunger will have a diameter or cross-section which enables it to do so. The plunger will typically be substantially or entirely hollow such that the contaminated needle can be shot back into the hollow interior of the plunger. However, it may also be possible to have the forward part of the plunger hollow (sufficiently to at least partially hold the needle) and the rear part solid or of different design. It is also envisaged that the plunger need not be hollow and may comprise an X type cross-section, or other cross-section such that the contaminated needle can pass into the passageway which is defined between the cross-section and the internal wall of the syringe. Other configurations of the plunger are envisaged providing that space is provided by the inside the plunger or between the plunger and the syringe body to accommodate the contaminated needle after the shoot back mechanism is triggered. However, it is considered useful that the plunger comprises a hollow cylindrical member.

The plunger has a front face which is the part of the plunger that extends into the syringe body and is pushed towards the front of the syringe. If the plunger is cylindrical, the front face will also be substantially cylindrical. A seal is provided over the front face of the plunger. The seal is of the type that can be pierced or broken such that the contaminated needle can pierce through or pass by the seal when the shoot back mechanism is triggered. Various types of seals are envisaged including rubber seals, plastic seals, metallic seals, elastic seals, laminated seals and the like. The seal will typically extend entirely over the front face of the plunger although depending on the size of the needle and the needle body, the seal may pass only over a central portion or other portion of the plunger. It is however preferred that the seal extends entirely over the front face of the plunger. If desired, the seal may have a central portion that extends over the central portion of the plunger and which can be of a different design (typically thinner) to enable it to be pierced or broken more easily, and an edge portion that extends over the edge of the plunger and which may be thicker and more easily compressed or squashed, the reason for which will be described in greater detail below. The seal may also extend over the sides of the plunger to provide a good sealing effect and to also assist in sealing the plunger against the inside wall of the syringe body.

The syringe contains a needle holder that holds the needle. The needle holder will typically be attached inside and in the front area of the syringe body. The needle holder may comprise an inner part and an outer part which are attached to each other by a frangible portion. Thus, it is not preferred that the inner part and the outer part are engaged frictionally; instead, the inner part and the outer part are bonded or joined together via the frangible portion. This provides a more reliable action and minimises accidental release of the needle holder. The inner part may comprise a front portion and a rear portion and an intermediate body portion. The front portion may extend through the opening in the front of the syringe body. The intermediate body portion may comprise an elongate substantially cylindrical portion containing an internal passageway which communicates with the puncture needle. The rear portion may extend towards the plunger and may comprise a profile or have a projection or have any other configuration to assist in the piercing or breaking of the plunger seal. Typically, the rear portion will have an "arrowhead" type configuration.

A spring is provided to bias the needle holder towards the retraction or shoot back position. The spring may comprise a helical spring and the helical spring may extend about the intermediate body portion of the needle holder.

The outer part of the needle holder may comprise the part that holds the needle holder in position in the front part of the syringe body and against the bias of the spring. The outer part may comprise an annular member. The annular member may have an outer face that engages with the inner wall of the syringe body. The engagement may comprise frictional engagement, but may also comprise abutment of part of the outer face with a shoulder, recess, or other configuration of the syringe body.

The outer part of the needle holder will typically be positioned in a rear portion of the passageway that is in the front of the syringe body. Thus, the outer part will typically be able to be pushed along the passageway from the rear portion of the passageway towards the front portion of the passageway. This distance may be between 1 mm up to 20 mm depending on the size of the syringe. Movement of the outer part in this manner relative to the inner part will cause the frangible portion to break thereby releasing the inner part from the outer part and triggering the shoot back mechanism.

Pushing of the plunger to the front of the syringe will cause the plunger to engage with the outer part and to push the outer part along the passageway thereby breaking the frangible portion and triggering the shoot back mechanism.

The outer part will typically contain at least one raised portion/zone/area which is directed towards the front of the plunger, that is which is pointing inwardly into the syringe body. The raised portion etc may be formed integrally with the outer part or may be formed separately and attached thereto, or relative thereto. The raised portion may comprise a bump, a rib, a tooth, a "button", or any other type of configuration which will serve the purpose which will be described in greater detail below. It is preferred that the raised portion extends only partially about the outer part, or only partially about the inside of the syringe. The arrangement will typically be such that as the plunger is pushed forwardly, the plunger will contact the raised portion first before the rest of the outer part is contacted by the plunger. This provides several benefits including a reduction in the force required to trigger the shoot back mechanism. For instance, the arrangement can concentrate the initial force of the plunger into a smaller area (typically on the outer part of the needle holder) to cause this part to move forwardly to break the frangible portion in this area. It is found the once the frangible portion is at least partially broken, less force is required to entirely rake the outer part from the inner part.

It is preferred that the edge portion of the seal on the plunger is thickened and is also preferred that this portion is relatively compressible. The reason for this is that the edge portion will be the first point of contact with the raised portion of the outer part, and as this contact occurs, the edge portion is compressed before the frangible portion is broken. This compression enables the front of the plunger to be pushed more closely against the needle holder thereby reducing dead space prior to triggering the shoot back mechanism.

The shoot back mechanism has similarities to that described in our earlier PCT application PCT/AU01/00183 which is incorporated herein by cross-reference; U.S. patent application Ser. No. 10/181,950, filed Aug. 2, 2002 corresponds to PCT/AU01/00183, and such application matured into U.S. Pat. No. 6,994,690 on Feb. 7, 2006.

BRIEF DESCRIPTION OF THE DRAWINGS

A preferred embodiment of the invention will be described with reference to the following drawings in which.

DETAILED DESCRIPTION

Figure 1:
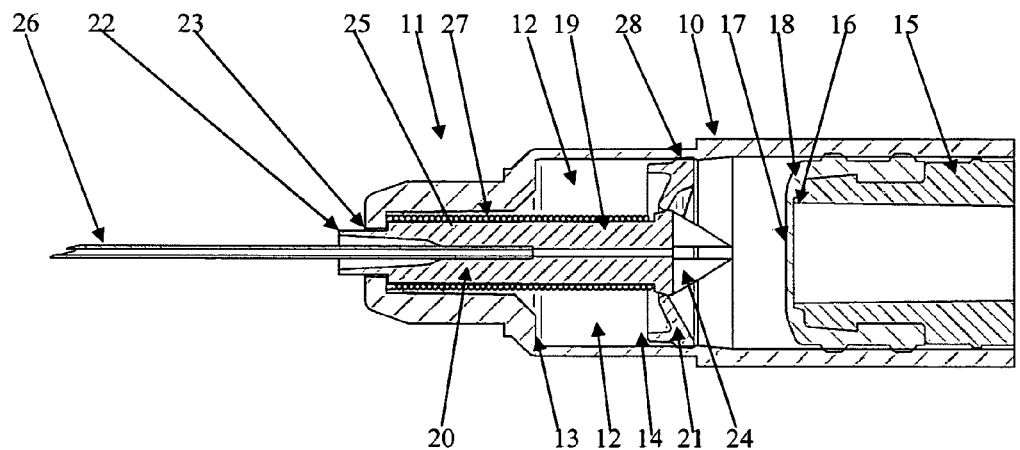
FIG. 1. Illustrates in cross-section a front portion of the syringe with the plunger moving towards the forward part of the syringe but not yet contacting any part of the shoot back mechanism.

Referring to the drawings and initially to FIG. 1, there is illustrated in cross-section the front part of a single use syringe. Briefly, the syringe comprises the following components: they syringe body 10 which has a front end area 11 which contains a longitudinal passageway 12, the passageway having a front portion 13 and a rear portion 14, a plunger 15 which is hollow and which contains a front face 16, a pierceable seal 17 which extends over the front face 16 of plunger 15, and which has a thickened edge portion 18, a needle holder 19 which comprises an inner part 20 and an outer part 21, the inner part further having a front portion 22 that extends through an opening 23 in the front of syringe body 11, a rear portion 24 which has an arrowhead type configuration, and an intermediate body portion 25, a needle (puncture needle) 26 that is fixed to the inner part 20, a spring 27 which extends about the intermediate body portion 25. Further more particular details will be described below.

The syringe body 10 has a front end area 11 which has a particular profile (see FIG. 1). The particular profile contains a forwardmost opening 23, a narrower diameter passageway behind opening 23 to contain part of the intermediate body portion 25, and a large diameter passageway 12, which essentially forms an extension of the internal bore of the syringe body through which the plunger 15 can pass.

The inner part 20 of the needle holder 19 cannot move through opening 23 (by virtue of intermediate body portion 25 having a larger diameter than the front portion 22 and this diameter being larger than opening 23). Thus, if the plunger 15 pushes against the inner part 20, inner part 20 cannot move.

One end of spring 27 abuts against the end of the narrower diameter passageway behind opening 23, and the other end of spring 27 abuts against a small shoulder just behind the arrowhead configuration of the rear portion 24 of inner part 20. With this configuration, the spring is compressed and biases the inner part 20 into the shoot back position which is inside the hollow interior of plunger 15. However, this is prevented by the inner part 20 being attached to the outer part 21.

Outer part 21 in the particular embodiment is annular in configuration and extends entirely about inner part 20 and in the area of the arrowhead configuration of the inner part, this being illustrated in FIG. 1. Outer part 21 has an outer face 28 which presses against the inside wall of passageway 12. A small abutment in the inside wall may be provided to positively position the outer part 21 in place, and to prevent the outer part from moving towards the plunger. The outer part is attached to the inner part by a frangible portion 29 which is referenced in FIG. 2. The frangible portion 29 in the particular embodiment extends entirely between the inner part and the outer part. This prevents fluid from leaking part the needle holder and into a forward part of passageway 12.

The outer part 21 contains a raised portion 30 (best illustrated in FIG. 2) but also illustrated in the other figures) which extends only partway (typically about quarter) about the outer part. The raised portion projects in the direction of plunger 15 and functions to reduce the pressure required to trigger the shoot back mechanism as will be described in greater detail below.

Figure 2:
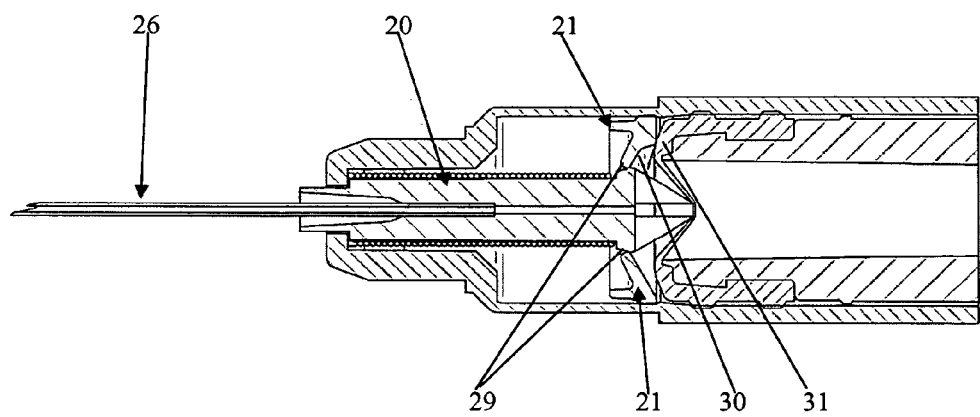
FIG. 2. Illustrates in cross-section the plunger just beginning to make contact with the raised portion of the outer part of the needle holder, and also just beginning to make contact with the "arrowhead" configuration on the inner part of the needle holder. At this stage, there is still an appreciable "dead space", and the shoot back mechanism has not yet been triggered.
Figure 3:
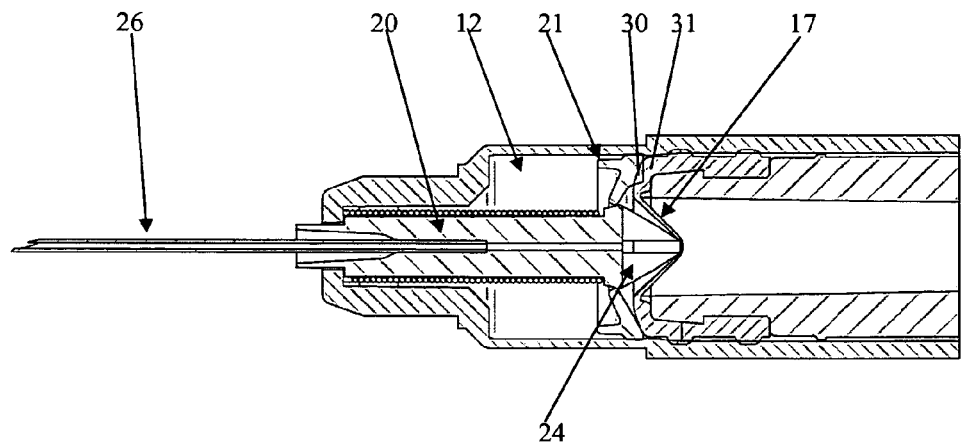
FIG. 3. Illustrates in cross-section the plunger having been pushed forwardly a little further than the position of FIG. 2, and illustrating the "arrowhead" configuration beginning to stretch the central part of the plunger seal, and also illustrating the plunger making greater contact with the outer part of the needle holder and having part of the plunger seal compressed to reduce the dead space. This position is just prior to triggering the shoot back mechanism.
Figure 4:
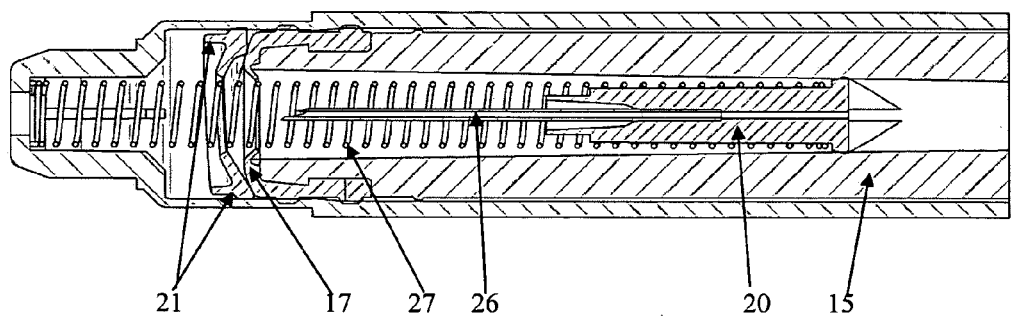
FIG. 4. Illustrates the syringe after the shoot back mechanism has been triggered with the contaminated needle (and the inner part of the needle holder) being safely within the confines of the plunger.

The triggering of the shoot back mechanism is somewhat similar to that described in our earlier international patent application given above, and basically occurs when plunger 15 is pressed hard up against the needle holder which is progressively illustrated in FIGS. 2-3. As this happens, the plunger contacts the outer part 21 and further forward pushing of the plunger enables the outer part to be pushed forwardly along passageway 12. As the inner part 20 of the needle holder cannot move in the same way, continued pressing on the plunger will cause the frangible portion 29 to be broken thereby releasing the inner part 20 from the outer part 21. As soon as this happens, spring 27 shoots the inner part 20 (containing the puncture needle 26) through the front of plunger 15 and into the hollow interior of the plunger. The final position is illustrated in FIG. 4.

However, in the present invention, a modification has been made to provide certain advantages. The modification includes providing the raised portion 30 on only a portion of the outer part 21. Thus, as plunger 15 moves forwardly from the position illustrated in FIG. 1 to the position illustrated in FIG. 2, an edge 31 of the plunger contacts the raised portion 30 (see FIG. 2). At this stage, the remainder of the plunger does not yet contact the remainder of the outer part 21; instead, only part (edge 31) of the plunger contacts only part (the raised portion 30) of the outer part. This concentrates the force of the plunger on to only part of the outer part 21 and enables the frangible portion in this area to be broken. It is found that once part of the frangible portion is broken, the remainder of the frangible portion can be broken with much less force.

However, there is a further modification which also reduces the dead space. The dead space is defined as the volume that cannot be expelled from the syringe due to the design of the internal components. Clearly, the amount of dead space should be reduced as much as possible.

In the present embodiment, once the plunger is in the position illustrated in FIG. 2, there is only slight contact between the edge 31 of the plunger and the raised portion 30 of the outer part. The arrowhead portion of the inner part has also contacted the seal 17 and is beginning to stretch the seal and weaken the seal. However, at this stage, the shoot back mechanism has not been triggered in that the frangible portion has not yet been stretched and broken.

Instead, the plunger is moved slightly more forwardly as indicated in FIG. 3. The forward movement need not be much (perhaps 1 mm), but is sufficient to bring the seal 17 into relatively close contact with the internal edges of the needle holder to reduce the amount of dead space. To accommodate the raised portion 30, the edge 31 of seal 17 is relatively thick (compared to the remainder of the front portion of the seal) and can be compressed or squashed. Therefore, in the position illustrated in FIG. 3, the plunger has been moved more forwardly and the raised portion 30 has been compressed into the rubbery edge 31 still without triggering the shoot back mechanism. It can be seen that in this particular position, the remainder of the front of the plunger is now in contact with the rest of the outer part 21. In this position, the amount of dead space has been reduced with respect to the amount of dead space when the plunger was in the position illustrated in FIG. 2.

Further forward movement of the plunger will now push the outer part 21 along passageway 12 and because of raised portion 30, the greatest force (and therefore greatest pushing action) will be on the raised portion 30 which will cause a preferential breaking or rupture of the frangible portion in this area only. This results in a reduced force being required to break the frangible portion. Once the frangible portion has been preferentially ruptured, it is found that less force is required to completely rupture the remainder of the frangible portion. As the plunger is pushed forwardly, the seal 17 is also stretched even further by the arrowhead configuration of the inner part 20 and the seal can be ruptured via the arrowhead configuration, or release of the spring is sufficient to now shoot the inner part and the contaminated needle through the seal and into the hollow plunger is illustrated in FIG. 4. The outer part 21 is slightly tilted as it is pushed forwardly.

The arrangement is found to reduce the force required to trigger the shoot back mechanism from approximately 9 kg to between 2-3 kg. The shoot back mechanism is still robust and has not been made "flimsy" in order to reduce the force required. This is achieved by having a raised portion on the outer part 21 and having the seal on the plunger being relatively conventional and not requiring any complicated design on the front of the plunger. By enabling the plunger to be relatively conventional, the raised portion 30 can be partially pushed into (compressed) into the edge of the seal to reduce the dead space prior to triggering the shoot back mechanism. It is not considered that such a relatively simple and reliable mechanism is possible with a complicated plunger shape.

Figure 5:
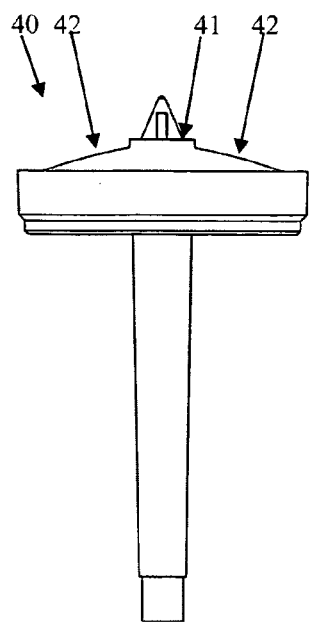
FIGS. 5-7. Illustrate a modified needle holder having shoulder portions (chamfers) to reduce dead space in the syringe.
Figure 6:
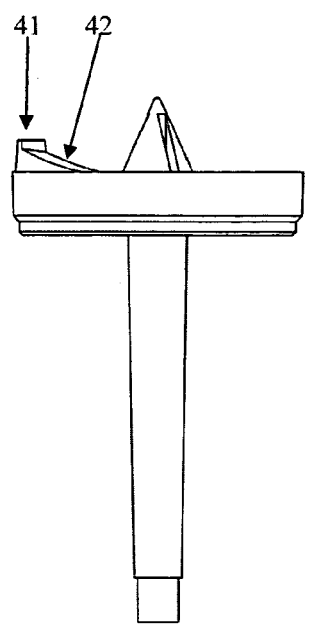
Figure 7:
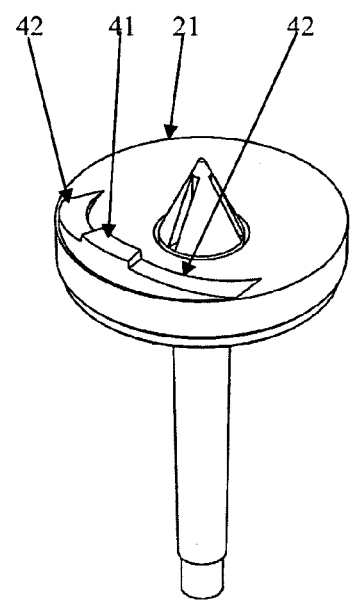

Referring to FIGS. 5-7, there is illustrated a modified needle holder 40 which is similar to that described above and which again contains an outer part 21 containing a raised portion 41, which is similar to the raised portion 30 described above except that raised portion 41 now additionally contains a pair of shoulder portions in the form of chamfers 42 which trail down to the face of outer portion 21. Chamfers 42 are formed integrally with raised portion 41. The arrangement is such that raised portion 41 comprises the "uppermost" part which initially contacts the plunger head and which allows the outer part to become dislodged from the inner part with reduced force. Therefore, and particularly as illustrated in FIG. 5, the raised portion 41 is profiled to be "higher" than the surrounding chamfers 42 such that dislodgement of outer part 21 can still occur on a relatively small surface area (that is the raised portion 41) and therefore with reduced force.

The function of chamfers 42 is to reduce the dead space which may otherwise occur between the plunger head and the needle holder. To explain, prior to the triggering the shoot back mechanism, the outer part 21 of the needle holder tips to one side and begins to break away from the inner portion. At this stage, and without the existence of chamfers 42, there would be a relatively large amount of dead space and therefore a relatively large amount of medication left in the barrel, immediately prior the triggering of the shoot back mechanism. By providing the chamfers, the dead space is reduced and the medication that would otherwise be left in the gap between the plunger and the needle holder is pushed through the needle.

Throughout the specification and the claims (if present), unless the context requires otherwise, the term "comprise", or variations such as "comprises" or "comprising", will be understood to apply the inclusion of the stated integer or group of integers but not the exclusion of any other integer or group of integers.

Throughout the specification and claims (if present), unless the context requires otherwise, the term "substantially" or "about" will be understood to not be limited to the value for the range qualified by the terms.

It should be appreciated that various other changes and modifications can be made to any embodiment described without departing from the spirit and scope of the invention. Thus, the appended claims should be broadly construed in a manner consistent with the spirit of applicant's unique invention, and should not be restricted to their literal terms.

I claim:

1. A single use syringe which comprises:
   a syringe body which contains a front end area containing a longitudinal passageway which has a front portion and a rear portion,
   a plunger which contains a front face which extends into the syringe body,
   a pierceable seal extending over the front face of the plunger,
   a needle holder that is attached inside and in the front area of the syringe body,
   a needle that is attached to the needle holder,
   a spring in the front of the syringe body and that is biased to shoot the needle holder through the pierceable seal in the front face of the plunger and into the plunger,
   the needle holder comprising an inner part and an outer part, the inner part containing the needle, the outer part engaging with a wall of the longitudinal passageway and initially in a rear portion of the passageway, a frangible portion between the inner part and the outer part, the frangible portion adapted to be broken to allow the needle holder to shoot into the plunger,
   the outer part containing a raised portion directed towards the seal of the plunger, the raised portion extending only partway about the outer part, the raised portion functioning to provide an initial contact area of the plunger with the outer part of the needle holder, thereby reducing the force required to break the frangible portion thereby allowing the needle holder to shoot through the seal.

2. The syringe of claim 1, wherein said front face contains an open central portion and an edge portion, the seal extending over the central portion and the edge portion.

3. The syringe of claim 2, wherein the edge portion of the seal on the plunger is thickened and is relatively compressible whereby upon pushing of the plunger towards the needle holder, the edge portion will be the first point of contact with the raised portion of the outer part, and as this contact occurs, the edge portion is compressed before the frangible portion is broken, the compression enabling the front of the plunger to be pushed more closely against the needle holder thereby reducing dead space prior to the needle holder shooting through the seal.

4. The syringe of claim 1, wherein the inner part of the needle holder has a front portion and a rear portion and an intermediate body portion, the front portion extending through the front portion of the syringe body, the intermediate body portion comprising an elongate substantially cylindrical portion containing an internal passageway which communicates with the needle, the rear portion extending towards the plunger and comprising a projection to assist in the piercing or breaking of the plunger seal.

5. The syringe of claim 4, wherein the projection has an arrowhead configuration.

6. The syringe of claim 1, wherein the outer part of the needle holder retains the inner part of the needle holder in position in the front portion of the syringe body and against the bias of the spring, the outer part comprising an annular member having an outer face that engages with the inner wall of the syringe body.

7. The syringe of claim 1, wherein the raised portion comprises a button.

8. The syringe of claim 1, wherein the seal on the plunger has a substantially flat front face.

9. The syringe of claim 1, wherein the raised portion contains an uppermost portion adapted for contact with the plunger, and at least one shoulder portion adjacent the uppermost portion which functions to reduce dead space between the front face of the plunger and the needle holder.

10. The syringe of claim 9, wherein said shoulder portion is positioned adjacent each side of the uppermost portion.

11. The syringe of claim 10, wherein the uppermost portion and the shoulder portion are formed integrally.

12. The syringe of claim 11, wherein the shoulder portion comprises a chamfer trailing down from the uppermost portion to the surfer of the outer part.

* * * * *